(12) United States Patent
Dam-Huisman et al.

(10) Patent No.: US 10,376,277 B2
(45) Date of Patent: Aug. 13, 2019

(54) SERRATED FORCEPS

(71) Applicant: CREA IP B.V., Dordrecht (NL)

(72) Inventors: Adriaantje Coliene Dam-Huisman, Delft (NL); Ferenc Kuhn, St. Johns, FL (US)

(73) Assignee: Crea IP B.V., Dordrecht (NL)

( * ) Notice: Subject to any disclaimer, the term of this patent is extended or adjusted under 35 U.S.C. 154(b) by 197 days.

(21) Appl. No.: 15/046,522

(22) Filed: Feb. 18, 2016

(65) Prior Publication Data
US 2017/0238956 A1 Aug. 24, 2017

(51) Int. Cl.
| | |
|---|---|
| A61B 17/28 | (2006.01) |
| A61B 17/30 | (2006.01) |
| A61F 9/007 | (2006.01) |
| A61B 17/00 | (2006.01) |
| A61B 17/29 | (2006.01) |
| A61B 90/00 | (2016.01) |

(52) U.S. Cl.
CPC ............ *A61B 17/30* (2013.01); *A61B 17/282* (2013.01); *A61F 9/00709* (2013.01); *A61B 2017/00455* (2013.01); *A61B 2017/2926* (2013.01); *A61B 2017/305* (2013.01); *A61B 2090/0811* (2016.02)

(58) Field of Classification Search
CPC .. A61F 9/007; A61F 9/00709; A61F 9/00736; A61B 17/29; A61B 17/30; A61B 2017/2926; A61B 2017/305
See application file for complete search history.

(56) References Cited

U.S. PATENT DOCUMENTS

| | | | | |
|---|---|---|---|---|
| 3,140,715 | A * | 7/1964 | Whitton, Jr. | A61B 17/30 294/106 |
| 3,515,139 | A * | 6/1970 | Mallina | A61B 17/282 606/207 |
| 3,815,609 | A * | 6/1974 | Chester | A61B 17/30 24/562 |
| 4,815,460 | A * | 3/1989 | Porat | A61B 17/282 294/902 |
| 4,991,567 | A * | 2/1991 | McCuen, II | A61B 17/0231 600/204 |
| 5,366,477 | A * | 11/1994 | LeMarie, III | A61B 17/29 403/336 |
| 6,013,088 | A | 1/2000 | Karavidas | |
| 6,887,240 | B1 * | 5/2005 | Lands | A61B 17/29 606/207 |
| 2004/0172057 | A1 * | 9/2004 | Guillebon | A61B 17/29 606/207 |
| 2006/0235466 | A1 * | 10/2006 | McGarity | A61B 17/02 606/205 |

(Continued)

*Primary Examiner* — Robert A Lynch
(74) *Attorney, Agent, or Firm* — N.V. Nederlandsch Octrooibureau; Catherine A. Shultz; Katelyn J. Bernier

(57) ABSTRACT

A forceps comprising a first jaw and a second jaw arranged along a longitudinal axis of the forceps for relative movement toward and away from one another. The first and second forceps jaws have respective first and second jaw surfaces facing each other. The first and second jaw surfaces have a serrated surface texture at least on a distal part thereof. A serration direction of the serrated surface texture is at an angle which is non-perpendicular to the longitudinal axis, resulting in additional profile structure elements at a tip portion surface, allowing to handle and manipulate fine tissue materials such as membranes in an eye.

18 Claims, 3 Drawing Sheets

(56) References Cited

U.S. PATENT DOCUMENTS

2008/0188877 A1     8/2008   Hickingbotham
2010/0092918 A1*   4/2010   Muller .................. A61B 17/30
                                                                                 433/159
2016/0296274 A1*   10/2016   Mensch ............. A61B 18/1442

* cited by examiner

SERRATED FORCEPS

FIELD OF THE INVENTION

The present invention relates to a forceps comprising a first jaw and a second jaw arranged along a longitudinal axis of the forceps for relative movement toward and away from one another, the first and second forceps jaws having respective first and second jaw surfaces facing each other.

PRIOR ART

American patent publication US2008/0188877 discloses a forceps intended for ocular surgery, having at least first and second jaws mounted for relative movement toward and away from one another. At the back side of the jaws, cutting elements are provided to allow to cut an exit wound upon withdrawal of the jaws from the eye. The gripping surfaces of the jaws are provided with a soft deformable material such as silicone to allow gripping an object in the eye.

American patent U.S. Pat. No. 6,013,088 discloses a surgical clamp with removable tips. The tips are provided with serrated teeth on inner surfaces of the tips, the serrated teeth being in the form of transverse ridges provided across a shortest length of the tips, i.e. perpendicular to a longitudinal direction of the surgical clamp.

SUMMARY OF THE INVENTION

The present invention seeks to provide an enhanced forceps, specifically suited to handle tissue material in eye surgery, such as membrane tissue.

According to the present invention, a forceps according to the preamble defined above is provided, the first and second jaw surfaces being provided with a serrated surface texture at least on a distal part thereof, wherein a serration direction of the serrated surface texture is at an angle which is non-perpendicular to the longitudinal axis. This ensures that at a tip portion surface of the forceps, serrated profile structure features are present in the form of teeth, allowing a better use and efficiency of the forceps, especially to handle and manipulate fine tissue materials such as membranes in an eye. In prior art forceps where a serrated texture is provided perpendicular to the axis of the forceps, the actual contact of the forceps with a membrane is small, sometimes even a single tooth of the serrated texture is grabbing the membrane. The present invention embodiments allow a very good grabbing functionality in all membrane positions during actual use. Further embodiments are described in the dependent claims as attached.

In a further aspect, the present invention relates to a method of manufacturing a forceps, the forceps comprising a first jaw and a second jaw arranged along a longitudinal axis of the forceps for relative movement toward and away from one another, the first and second forceps jaws having respective first and second jaw surfaces facing each other, the first and second jaw surfaces being provided with a serrated surface texture at least on a distal part thereof, wherein the serration direction of the serrated surface texture is at an angle non-perpendicular to the longitudinal axis, and wherein the serrated surface texture is provided using wire electrical discharge machining. This is very advantageous in providing a suitable textured profile with the desired structural and operational advantages.

SHORT DESCRIPTION OF DRAWINGS

The present invention will be discussed in more detail below, using a number of exemplary embodiments, with reference to the attached drawings, in which FIG. 1 shows a perspective view of a forceps according to an embodiment of the present invention;

DETAILED DESCRIPTION OF EXEMPLARY EMBODIMENTS

Forceps are surgical instruments widely used in many surgery applications. The present invention embodiments of the forceps described below and subject of the attached claims are especially suited for use as a micro-forceps in ophthalmology applications, such as removing and handling of membrane tissue inside the eye.

Figure 1:
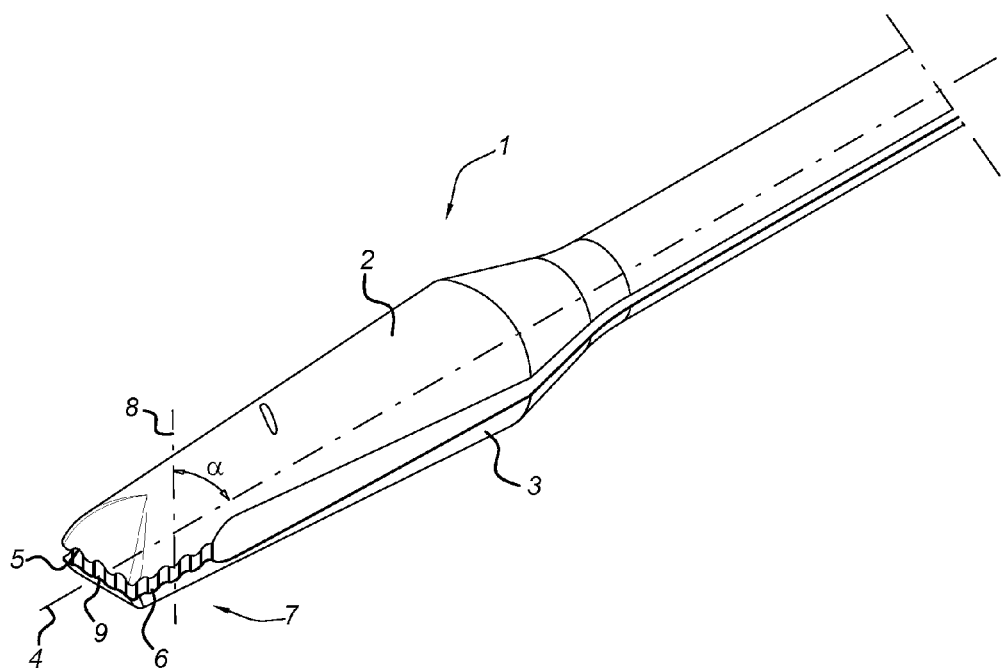

FIG. 1 shows a perspective view of the operational part of the forceps 1 according to an embodiment of the present invention. As shown, the forceps 1 comprises a first jaw 2 and a second jaw 3 arranged along a longitudinal axis 4 of the forceps 1 for relative movement toward and away from one another. The first and second forceps jaws 2, 3 have respective first and second jaw surfaces 5, 6 facing each other. The first and second jaw surfaces 5, 6 are provided with a serrated surface texture at least on a distal part 7 of the forceps 1. The serrated surface texture can be provided as a surface with grooves and ridges. A serration direction 8 of the serrated surface texture is at an angle α which is non-perpendicular to the longitudinal axis 4.

The angled serrated texture on the opposing surfaces 5, 6 allows to provide a (micro-)forceps 1 which is very good to handle during actual use, and can provide very good grip on tissue to be handled. The fine teeth on a tip portion surface 9 resulting from the serrated texture also allows to have also a very fine pitched gripping feature for the forceps 1. It is noted that in prior art micro-forceps, the distal end has a smooth surface, whereas the present invention forceps provides additional gripping teeth. Especially when handling membrane tissue inside the eye, such a combined handling and gripping function is very advantageous, as some operations can be executed using only a single forceps 1.

The angle α between the longitudinal axis 4 and serration direction 8 is different from 0 and 90 degrees, e.g. between 10 and 80 degrees in a further embodiment, and as shown in the embodiments shown herein, the angle α is at about 45 degrees. Such configurations still provide a very good normal forceps functionality, as well as the additional finer pitched teeth at the tip portion surface 9.

Figure 2:
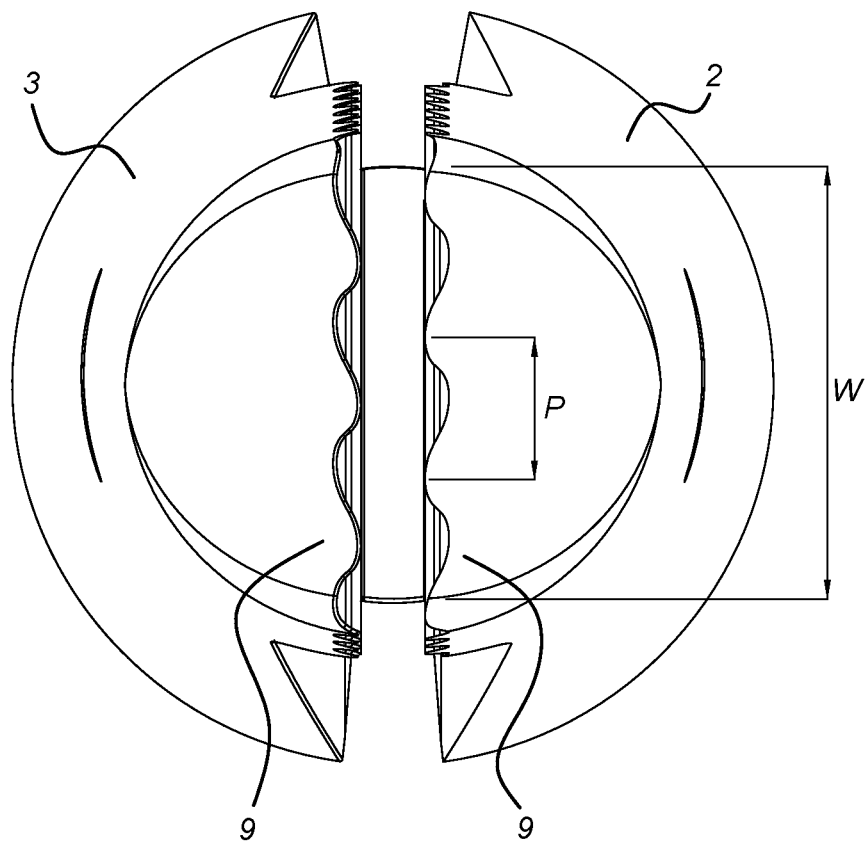
FIG. 2 shows a front view of the forceps shown in FIG. 1.

The present invention embodiments could also be defined as the forceps having the feature that the first and second forceps jaws 2, 3 have a blunt shaped tip portion surface 9 at a distal end or tip portion of the forceps 1, and that the serrated surface texture on the opposing surfaces 5, 6 forms at least two serrations (i.e. teeth shaped gripping elements) at the blunt shaped tip portion surface 9. The number of serrations provided is of course a function of the dimensions of the forceps 1 (width w of first and second jaw 2, 3), the angle α between serration direction 8 and longitudinal direction 4, and the serration pitch p. To have at least two gripping teeth at the tip portion surface, the pitch p should then be at most the half of the width w (p<½ w). In a further embodiment, at least three serrations are provided at the tip portion surface 9 (p<⅓ w). This is shown clearly in the front view of the forceps as shown in FIG. 2, which shows the pitch p of the serrations, and width w of the blunt shaped tip portion surface 9. Although the embodiments of the present invention shown in the figures have a blunt shaped tip portion surface which is generally flat, also embodiments may be foreseen having a rounded tip portion surface 9.

As shown in the embodiment of FIGS. 1 and 2, the serrated surfaces 5, 6 of the first and second forceps jaws 2, 3 are arranged to provide interlocking grip surfaces, to allow a firm and good gripping function of the forceps 1.

The serrated surface texture may comprise a semi-sinusoidal cross sectional profile, i.e. a wavelike cross sectional profile resembling a sine wave, wherein the surfaces of the first and second jaw 2, 3 are moved 180 degree out of phase (i.e. a ridge on the first jaw surface 5 is directly opposing a groove on the second jaw surface 6). In a further advantageous embodiment, the semi-sinusoidal cross sectional profile has sharp ridges and smooth, rounded grooves, which enhances the gripping capabilities of the forceps 1 (see embodiment described with reference to FIG. 3-5 below). As alternative embodiments, the serrated surface texture may comprises a sinusoidal cross sectional profile (full sinusoidal wave form, see embodiment of FIGS. 1 and 2), a triangular cross sectional profile, a saw tooth cross sectional profile or a trapezoidal cross sectional profile.

Figure 3:
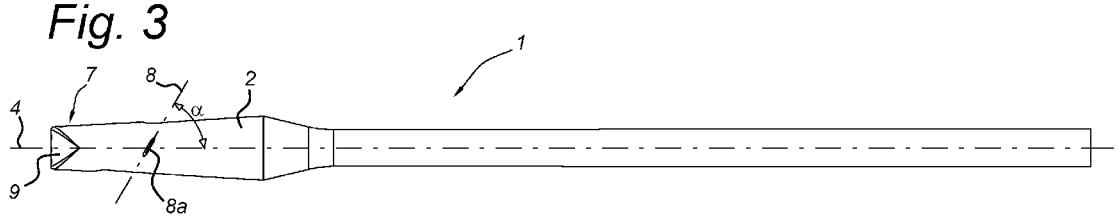
FIG. 3 shows a top view of a forceps according to an embodiment of the present invention.
Figure 4:
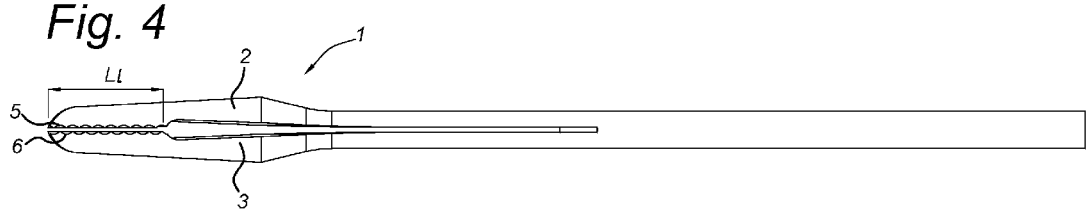
FIGS. 4 and 5 show opposing side views of the forceps shown in FIG. 3.
Figure 5:
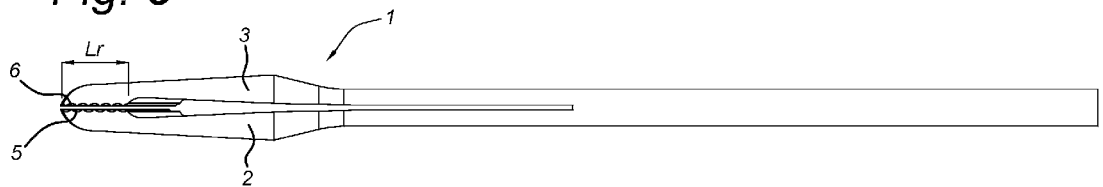

FIGS. 3, 4 and 5 show a top view and opposing side views of a further embodiment of the present invention forceps 1. The same elements and features of the embodiment discussed in relation to FIG. 1 are indicated here with the same reference numerals.

In the top view of FIG. 3, and additional marker 8a is shown, providing an indication of the serration direction 8 to the user of the forceps 1, allowing to use the proper tip part of the forceps 1 for specific purposes such as gripping and handling an extreme fine piece of tissue.

The side views of FIGS. 4 and 5 also clearly show that the cross sectional profile of the serrated surface texture comprises is semi-sinusoidal as discussed above, i.e. having sharp ridges and smooth grooves.

From FIGS. 4 and 5, it is furthermore clarified that the opposing surface 5, 6 need not be rectangular surfaces. In this embodiment it is shown that the serrated surface parts are provided on the opposing surface along the serration direction. This is indicated by the left serration length $L_l$ shown in FIG. 4, which is longer than the right serration length $L_r$ shown in FIG. 5. FIG. 5 also clearly shows the first ridges of the serrated surface texture are running askew, i.e. under a 45 degree angle.

The first and second forceps jaws 2, 3 (or in a further embodiment the entire forceps 1) comprise a metal material, such a stainless steel (i.e. medical grade steel) or titanium, a ceramic material, or a plastic material.

As mentioned, the forceps according to the present invention embodiments is particularly suited for ophthalmological applications, and is provided as a micro-forceps with a dimension of 20 gauge (0.91 mm outer diameter), 23 gauge (0.64 mm outer diameter), 25 gauge (0.51 mm outer diameter) or even 27 gauge (0.41 mm outer diameter).

Manufacturing of the present invention embodiments of the forceps 1 can be achieved in various manners, usually by using manufacturing techniques known as such depending on the base material(s) used. In a specifically advantageous embodiment, the serrated surface texture is provided using wire electrical discharge machining, which is also known in the field as spark machining, or spark eroding. This technique provides for obtaining the desired depth and surface texture in a proper and efficient manner, e.g. to obtain the semi-sinusoidal or sinusoidal cross sectional profile as discussed above. As alternative or additional manufacturing steps for providing the textured surfaces on the opposing faces 5, 6 of the first and second jaw 2, 3, one or more from roll forming, press forming, casting, molding may be used.

The present invention embodiments have been described above with reference to a number of exemplary embodiments as shown in the drawings. Modifications and alternative implementations of some parts or elements are possible, and are included in the scope of protection as defined in the appended claims.

The invention claimed is:

1. A forceps comprising a first jaw and a second jaw arranged such that a longitudinal axis of the first and second jaws lies along a longitudinal axis of the forceps, the first and second jaws being arranged for relative movement toward and away from one another, the first and second forceps jaws having respective first and second jaw surfaces facing each other, the first and second jaw surfaces being provided with a serrated surface texture at least on a distal part thereof, wherein the serrated surface texture is a surface provided with grooves and ridges, and a serration direction along the grooves and ridges of the serrated surface texture is at an angle which is non-perpendicular to the longitudinal axis of the jaws, and wherein the first and second forceps jaws have a blunt shaped tip portion surface providing a flat distal end and two opposing sides, and wherein the serrated surface texture forms at least three teeth at the flat distal end of the blunt tip shaped portion surface and a plurality of teeth at each opposing side, wherein the forceps comprises a marker on an outer surface of at least one jaw that indicates the serration direction.

2. The forceps of claim 1, wherein the angle is between 10 and 80 degrees.

3. The forceps of claim 1, wherein the angle is 45 degrees.

4. The forceps of claim 1, wherein the serrated surfaces of the first and second forceps jaws are arranged to provide interlocking grip surfaces.

5. The forceps of claim 1, wherein the serrated surface texture comprises a semi-sinusoidal cross-sectional profile.

6. The forceps of claim 1, wherein the serrated surface texture comprises a profile selected from the group consisting of:
a sinusoidal cross-sectional profile,
a triangular cross-sectional profile,
a saw tooth cross-sectional profile, or
a trapezoidal cross-sectional profile.

7. The forceps of claim 1, wherein the first and second forceps jaws comprise a metal material, a ceramic material, or a plastic material.

8. The forceps of claim 1, wherein the forceps is a micro forceps having a dimension of 20, 23, 25 or 27 gauge.

9. The forceps of claim 1, wherein the first and second forceps jaws comprise titanium or stainless steel.

10. The forceps of claim 1, wherein the grooves have a smooth rounded profile and the ridges have a sharp profile.

11. A method of manufacturing forceps, the method comprising the steps of:

attaching a first jaw and a second jaw to each other such that the first and second jaws are arranged such that a longitudinal axis of the first and second jaws lies along a longitudinal axis of the forceps, the first and second jaws being arranged for relative movement toward and away from one another, forming, in first and second opposing jaw surfaces of the first and second forceps jaws respectively, the first and second jaw surfaces being formed with a serrated surface texture at least on a distal part thereof, wherein the serrated surface texture is a surface provided with grooves and ridges, and a serration direction along the grooves and ridges of the serrated surface texture is at an angle non-perpendicular to the longitudinal axis of the jaws, and wherein the first and second forceps jaws have a blunt shaped tip portion surface providing a flat distal end and two opposing sides, and wherein the serrated surface texture forms at least three teeth at the flat distal end of the blunt tip shaped portion surface and a plurality of teeth at each opposing side wherein the serrated surface is provided on the opposing surfaces of the first and second jaws and extends a first length along a first edge of the opposing surfaces and a second length along a second edge of the opposing surfaces, wherein the first length is longer than the second length such that the serrated surface is non-rectangular.

12. A forceps comprising a first jaw and a second jaw arranged such that a longitudinal axis of the first and second jaws lies along a longitudinal axis of the forceps, the first and second jaws being arranged for relative movement toward and away from one another, the first and second forceps jaws having respective first and second jaw surfaces facing each other, the first and second jaw surfaces being provided with a serrated surface texture at least on a distal part thereof, wherein the serrated surface comprises alternating grooves and ridges extending across the first and second jaw surfaces, and a serration direction along the grooves and ridges of the serrated surface texture is at an angle which is non-perpendicular to the longitudinal axis of the jaws, and wherein the first and second forceps jaws have a blunt shaped tip portion surface providing a flat distal end and two opposing sides, and wherein the serrated surface texture forms at least three teeth at the flat distal end of the blunt tip shaped portion surface and a plurality of teeth at each opposing side wherein the serrated surface is provided on the opposing surfaces of the first and second jaws and extends a first length along a first edge of the opposing surfaces and a second length along a second edge of the opposing surfaces, wherein the first length is longer than the second length such that the serrated surface is non-rectangular.

13. The forceps of claim 12, wherein the angle is between 10 and 80 degrees to the longitudinal axis of the forceps.

14. The forceps of claim 12, wherein the angle is 45 degrees to the longitudinal axis of the forceps.

15. The forceps of claim 12, wherein the serrated surfaces of the first and second forceps jaws are arranged to provide interlocking grip surfaces.

16. The forceps of claim 12, wherein the serrated surface texture comprises a profile selected from the group consisting of:
   a sinusoidal cross-sectional profile,
   a semi-sinusoidal cross-sectional profile
   a triangular cross-sectional profile,
   a saw tooth cross-sectional profile,
   a trapezoidal cross-sectional profile.

17. The forceps of claim 12, wherein the first and second forceps jaws comprise a metal material, a ceramic material, or a plastic material.

18. The forceps of claim 12, wherein the forceps is a micro forceps having a dimension of 20, 23, 25 or 27 gauge.

* * * * *